# (12) United States Patent
Surtees et al.

(10) Patent No.: US 8,338,621 B2
(45) Date of Patent: Dec. 25, 2012

(54) PROCESS FOR THE PREPARATION OF 2-OXO-1-PYRROLIDINE DERIVATIVES

(75) Inventors: John Surtees, Overijse (BE); Didier Bouvy, Ottignies (BE); Antoine Thomas, Lannoy (FR); Yves Combret, Oye Plage (FR); Michael Frank, Buchs (CH); Gunther Schmidt, Aarau (CH); Guy Duchene, Sterrebeek (BE)

(73) Assignee: UCB S.A., Brussels (BE)

( * ) Notice: Subject to any disclaimer, the term of this patent is extended or adjusted under 35 U.S.C. 154(b) by 950 days.

(21) Appl. No.: 11/612,654

(22) Filed: Dec. 19, 2006

(65) Prior Publication Data
US 2008/0009638 A1    Jan. 10, 2008

Related U.S. Application Data

(60) Provisional application No. 60/754,070, filed on Dec. 21, 2005.

(51) Int. Cl.
*C07D 207/04*    (2006.01)
(52) U.S. Cl. ...................................... 548/550
(58) Field of Classification Search .................. 548/550
See application file for complete search history.

(56) References Cited

U.S. PATENT DOCUMENTS 7,122,682 B2 * 10/2006 Ates et al. ..................... 548/543
7,563,912 B2 * 7/2009 Ates et al. ..................... 548/543

FOREIGN PATENT DOCUMENTS

WO      03/014080 A2   2/2003
WO   WO 03/014080    *   2/2003

OTHER PUBLICATIONS

March's Advanced Organic Chemistry, 5th ed., (2001) chapter 10.*
McMurray (Organic Chemistry, 5th ed. (2000), Brooks/Cole, 1284 pages), pp. 390-401 provided.*
Kenda, Benoit M., et al., "Discovery of 4-Substituted Pyrrolidone Butanamides as New Agents with Significant Antiepileptic Activity," J. Med. Chem., 2004, 47, pp. 530-549.
Bastock, Tony, et al., "Bromination and Production Techniques for Fine Chemicals," Specialty Chemicals Magazine, Feb. 2004, pp. 32-33.
Orlova, N.A., et al., "Reaction of N-Silylated Lactmas with a-bromocarboxylic Acid Esters," Zhurnal Obshchei Khimii, 1992, 62(10), pp. 2277-2281.
Boschi, Francesca, et al., "A Synthesis of Levetiracetam Based on (S)-N-Phenylpantolactam as a Chiral Auxiliary," Science Direct, 2005, pp. 3739-3745.
Streitwieser et al., Introduction to Organic Chemistry, 3rd. Edition, McMillan Publishing Co., NY, 1985, pp. 501 & 373.
Cram, D., "Structure of Carbanions", Pure Appl. Chem., 1963, vol. 7 (2-3), pp. 155-172.
Smith et al., "Reactions, Mechanisms, and Structure", March's Advanced Organic Chemistry, 5th ed. (2001), Books/Cole, pp. 327-331, 548-551, and 763-767.

* cited by examiner

*Primary Examiner* — Robert Havlin
(74) *Attorney, Agent, or Firm* — McDonnell Boehnen Hulbert & Berghoff LLP

(57) ABSTRACT

The present invention relates to alternative processes for the preparation of 2-oxo-1-pyrrolidine derivatives of formula (I)

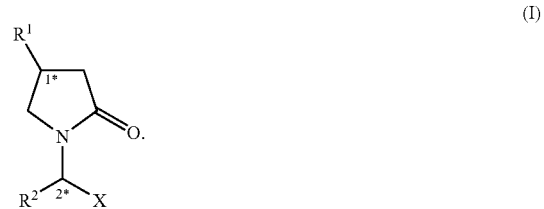

Particularly, the present invention relates to alternative processes for the synthesis of levetiracetam, brivaracetam and seletracetam.

10 Claims, No Drawings

PROCESS FOR THE PREPARATION OF 2-OXO-1-PYRROLIDINE DERIVATIVES

This application claims the benefit of U.S. Provisional Application Ser. No. 60/754,070 filed Dec. 21, 2005.

The present invention relates to alternative processes for the preparation of 2-oxo-1-pyrrolidine derivatives.

European Patent No. 0 162 036 B1 discloses compound (S)-2-(2-oxopyrrolidin-1-yl)butanamide, which is known under the International Non-proprietary Name of Levetiracetam.

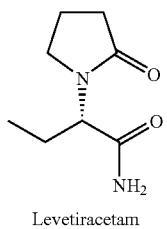

Levetiracetam

Levetiracetam is disclosed as a protective agent for the treatment and prevention of hypoxic and ischemic type aggressions of the central nervous system in European patent EP 0 162 036 B1. This compound is also effective in the treatment of epilepsy.

The preparation of Levetiracetam has been disclosed in European Patent No. 0 162 036 and in British Patent No. 2 225 322.

International patent application having publication number WO 01/62726 discloses 2-oxo-1-pyrrolidine derivatives and methods for their preparation. It particularly discloses compound (2S)-2-[(4R)-2-oxo-4-propyl-pyrrolidin-1-yl] butanamide known under the international non propriety name of brivaracetam.

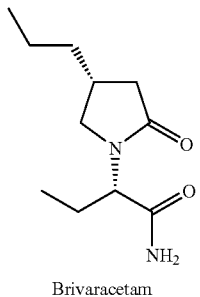

Brivaracetam

International patent application having publication number WO 2005/121082 describes a process of preparation of 2-oxo-1-pyrrolidine derivatives and particularly discloses a process of preparation of (2S)-2-[(4S)-4-(2,2-difluorovinyl)-2-oxo-pyrrolidin-1-yl]butanamide known under the international non propriety name of seletracetam.

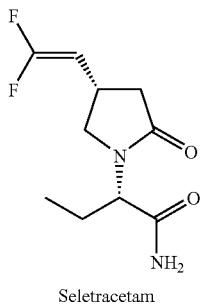

Seletracetam 2-oxo-1-pyrrolidine derivatives are therefore particularly useful in the pharmaceutical industry.

In the course of known processes for the preparation of 2-oxo-1-pyrrolidine derivatives, one or more stereoisomers of these derivatives may be generated and thus one or more separation steps of these stereoisomers are required in order to obtain the desired compound. These separation steps may lower the overall yield of the process and are generally time- and cost-consuming.

There is thus a need to provide an alternative process for the synthesis of 2-oxo-1-pyrrolidine derivatives.

In a first aspect, the present invention relates to a process for the preparation of a compound of formula (I),

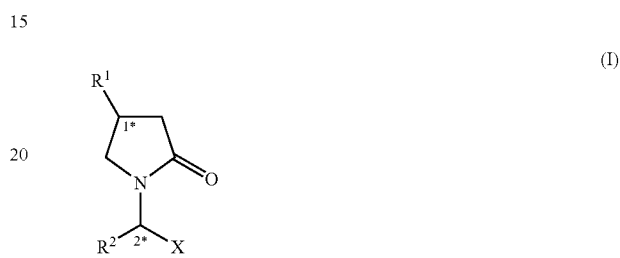

wherein,
$R^1$ is hydrogen, $C_{1-10}$ alkyl or $C_{2-6}$ alkenyl
$R^2$ is $C_{1-10}$ alkyl or $C_{2-6}$ alkenyl,
X is —$CONR^4R^5$, —COOH, —$COOR^3$ or —CN,
$R^3$ is $C_{1-10}$ alkyl;
$R^4$ is hydrogen or $C_{1-10}$ alkyl;
$R^5$ is hydrogen or $C_{1-10}$ alkyl;
which process comprises reacting a substantially optically pure compound of formula (II),

wherein
$R^2$ is as defined here above for compound of formula (I),
$X^1$ is as defined here above for X in compound of formula (I), and
Y is a leaving group selected from halogen, sulfonate group or —$N_2^+$,
with a compound of formula (III), or salts thereof,

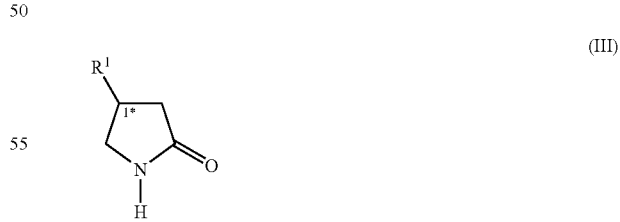

wherein $R^1$ is as defined here above for compound of formula (I).

This process advantageously minimizes the number of separation steps required to obtain the desired 2-oxo-1-pyrrolidine derivatives.

The expression "substantially optically pure" as used herein in the specification when referring to a particular compound comprising one stereogenic center means that at least 95%, preferably at least 96%, more preferably at least 97%, most preferably at least 98%, even most preferably at least 99% of the compound has the stereogenic center indicated by (1*), (2*) or (3*) in a given configuration (R) or (S).

The term "alkyl", as used herein, is a group which represents saturated, monovalent hydrocarbon radicals having straight (unbranched), branched or cyclic moieties, or combinations thereof. Preferred alkyl comprises 1 to 10 carbons. More preferred alkyl comprises 1 to 4 carbons. Optionally, alkyl groups may be substituted by 1 to 5 substituents independently selected from the group consisting of halogen, hydroxy, alkoxy, ester, acyl, cyano, acyloxy, acid, amide or amino group. Preferred alkyl groups are methyl, ethyl, n-propyl, trifluoromethyl and trifluoroethyl.

The term "alkenyl" as used herein represents unsubstituted or substituted branched, unbranched or cyclic hydrocarbon radicals or combinations thereof having at least one double bond. Preferred alkenyl comprises 2 to 6 carbons. More preferred alkenyl comprises 2 to 4 carbons. "Alkenyl" moieties may be optionally substituted by 1 to 5 substituents independently selected from the group consisting of halogen, hydroxy, alkoxy, ester, acyl, cyano, acyloxy, carboxylic acid, amide or amino group.

The term "halogen", as used herein, represents an atom of fluorine, chlorine, bromine, or iodine.

The term "hydroxy", as used herein, represents a group of formula —OH.

The term "alkoxy", as used herein, represents a group of formula —OR$^a$ wherein R$^a$ is C$_{1-4}$ alkyl as defined above.

The term "acyl" as used herein, represents a group of formula R$^b$CO—, wherein R$^b$ represents a C$_{1-4}$ alkyl as defined above.

The term "ester", as used herein, represents a group of formula —COOR$^c$ wherein R$^c$ represents a C$_{1-4}$ alkyl as defined above.

The term "cyano" as used herein represents a group of formula —CN.

The term "acyloxy" as used herein represents a group of formula —O—COR$^d$, wherein R$^d$ is a C$_{1-4}$ alkyl as defined above or an aryl group.

The term "aryl" as used herein, represents an organic radical derived from an aromatic hydrocarbon by removal of one hydrogen, for example a phenyl.

The term "carboxylic acid" as used herein represents a group of formula —COOH.

The term "amino group", as used herein, represents a group of formula —NH$_2$, NHR$^e$ or NR$^f$R$^e$ wherein R$^e$ and R$^f$ are alkyl groups as defined above in the specification.

The term "amide", as used herein, refers to a group of formula —CO—NH$_2$, —CO—NHR$^g$, or —CO—NR$^g$R$^h$, wherein R$^g$ and R$^h$ are alkyl groups as defined above in the specification.

The term "leaving group", as used herein, has the same meaning by the person skilled in the art (Advanced Organic Chemistry: reactions, mechanisms and structure—Third Edition by Jerry March, John Wiley and Sons Ed.; 1985 page 179) and represents a group which is part of and attached to a substrate molecule; in a reaction where the substrate molecule undergoes a displacement reaction (with for example a nucleophile), the leaving group is then displaced.

The term "sulfonate group" as used herein represents a group of formula —O, —SO$_2$—R$^i$ wherein R$^i$ is an alkyl or an aryl as defined hereabove in the specification. Preferred sulfonate groups are methanesulfonate, para-toluenesulfonate group or trifluoromethanesulfonate.

In one embodiment according to first aspect of the present invention, R$^1$ is C$_{1-10}$ alkyl or C$_{2-6}$ alkenyl. In another embodiment, according to first aspect of the present invention, R$^1$ is C$_{1-4}$ alkyl or C$_{2-4}$ alkenyl. In a further embodiment according to first aspect of the present invention, R$^1$ is n-propyl or 2,2-diflurorovinyl.

In one embodiment according to first aspect of the present invention, R$^2$ is C$_{1-4}$ alkyl. In another embodiment according to first aspect of the present invention, R$^2$ is ethyl.

In one embodiment according to first aspect of the present invention, X is —CONR$^4$R$^5$, —COOH or —COOR$^3$, wherein R$^3$ is a C$_{1-4}$ alkyl. In another embodiment according to first aspect of the present invention, X is —CONR$^4$R$^5$.

In one embodiment according to first aspect of the present invention, X$^1$ is —CONR$^4$R$^5$ or —COOR$^3$, wherein R$^3$ is a C$_{1-4}$ alkyl. In another embodiment according to first aspect of the present invention, X$^1$ is COOR$^3$, wherein R$^3$ is a C$_{1-4}$ alkyl.

In one embodiment according to first aspect of the present invention, X$^2$ is —CONR$^4$R$^5$ or —COOR$^3$, wherein R$^3$ is a C$_{1-4}$ alkyl. In another embodiment according to first aspect of the present invention, X$^2$ is COOR$^3$, wherein R$^3$ is a C$_{1-4}$ alkyl.

In a particular embodiment, R$^3$ is methyl.

In one embodiment according to first aspect of the present invention, R$^4$ is hydrogen or C$_{1-4}$ alkyl. In another embodiment according to first aspect of the present invention, R$^4$ is hydrogen.

In one embodiment according to first aspect of the present invention, R$^5$ is hydrogen or C$_{1-4}$ alkyl. In another embodiment according to the first aspect of the present invention, R$^5$ is hydrogen.

In one embodiment according to first aspect of the present invention, Y is a halogen or a sulfonate group. In another embodiment according to first aspect of the present invention, Y is bromine, a methanesulfonate or a trifluoromethanesulfonate group.

In one embodiment according to the first aspect of the present invention, at least 95%, preferably at least 96%, more preferably at least 97%, most preferably at least 98%, even most preferably at least 99% of compound of formula (II) has the stereogenic center indicated by (2*) in configuration (R).

Salts of compound of formula (III) are preferably alkali metal salts, for example, sodium, potassium or lithium salt.

The reaction of compound of formula (II) with compound of formula (III) generally occurs in the presence of a base.

Examples of bases which may be used in the processes according to the present invention are potassium hydride, sodium hydride, sodium methoxide, potassium methoxide, sodium isopropoxide, sodium tert-butoxide and potassium tert-butoxide.

The reaction may be performed using compound of formula (III) as solvent or alternatively in another solvent.

Examples of solvents which may be used according to the present invention are methanol, isopropanol, tert-butanol, dimethoxyethane, dimethylsulphoxide, dichloromethane, acetonitrile and toluene or mixtures thereof.

The process according to the present invention is generally achieved at a temperature ranging from 0° C. to 100° C., preferably ranging from 0° C. to 70° C., more preferably ranging from 0° C. to 20° C.

Compound of formula (I), wherein X is —CO—NR$^4$R$^5$ may be obtained directly by reacting compound of formula (II), wherein X$^1$ is —CO—NR$^4$R$^5$, with compound of formula (III).

Alternatively, compound of formula (II) wherein X$^1$ is COOR$^3$ or COOH may be reacted with compound of formula (III), or salts thereof, to afford compound of formula (V),

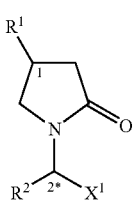

(V)

wherein
$R^1$ and $R^2$ are as defined for compound of formula (I);
$X^1$ is $COOR^3$ and COOH;
$R^3$ is $C_{1-10}$ alkyl.

Compound of formula (V) may be further converted to compound of formula (I), wherein X is —CO—$NR^4R^5$, according to conventional methods known to the man skilled in the art or according to one of the methods described in international patent application published under number WO 03/014080.

For example, compound of formula (I) may be obtained by ammonolysis of compound of formula (V). Said ammonolysis may be performed in the presence of water according to conditions described in international patent application published under number WO 03/014080. When $R^1$ is different from hydrogen, compounds of formula (I) and compounds of formula (V) have at least two stereogenic centers in their structure which are indicated by (1*) and (2*). These stereogenic centers may be present in R or S configuration, said R and S notation being used in accordance with the rules described in Pure. Appl. Chem., 45 (1976) 11-30.

Compounds of formula (I) and compounds of formula (V) may be independently a mixture of diastereoisomers.

Preferably, compounds of formula (I) and compounds of formula (V) are independently a mixture of epimers.

The term "epimers" as used herein, when referring to diastereoisomers, is defined as two diastereoisomers having only one stereogenic center in a different configuration one from another.

Most preferably compounds of formula (I) and compounds of formula (V) are independently a mixture of epimers with respect to stereogenic center (1*).

Said mixture may comprise the epimers in a ratio equal to 1. Advantageously, said mixture comprises epimers in a ratio different from 1.

In a particular embodiment, compounds of formula (I) and compounds of formula (V) according to the present invention are diastereoisomerically enriched.

The expression "diastereoisomerically enriched" as used herein when referring to a particular compound means that at least 95%, preferably at least 96%, more preferably at least 97%, most preferably at least 98%, even most preferably at least 99% of the compound has the stereogenic center indicated by (2*) in a given configuration (R) or (S) and that more than 50%, preferably more than 75%, more preferably more than 85%, most preferably more than 94% of the compound has the stereogenic center indicated by (1*) in a given configuration (R) or (S).

Preferably, at least 95%, preferably at least 96%, more preferably at least 97%, most preferably at least 98%, even most preferably at least 99% of compound of formula (I) or of compound of formula (V) has the stereogenic center indicated by (2*) in configuration (S).

More preferably, compounds of formula (I) and compounds of formula (V) according to the present invention are substantially diastereoisomerically pure.

The expression "substantially diastereoisomerically pure" as used herein when referring to a particular compound means that at least 95%, preferably at least 96%, more preferably at least 97%, most preferably at least 98%, even most preferably at least 99% of the compound has the stereogenic center indicated by (2*) in a given configuration (R) or (S) and that at least 95%, preferably at least 96%, more preferably at least 97%, most preferably at least 98%, even most preferably at least 99% of the compound has the stereogenic center indicated by (1*) in a given configuration (R) or (S).

Substantially diastereoisomerically pure compound of formula (I) may be obtained by reacting a substantially optically pure compound of formula (II) with a substantially optically pure compound of formula (III).

Thus, in a particular aspect, the present invention relates to a process for the preparation of substantially diastereoisomerically pure compound of formula (I),

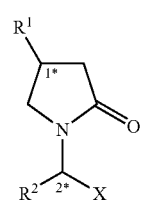

(I)

wherein,
$R^1$ is $C_{1-10}$ alkyl or $C_{2-6}$ alkenyl
$R^2$ is $C_{1-10}$ alkyl or $C_{2-6}$ alkenyl,
X is —$CONR^4R^5$, —COOH, —$COOR^3$ or —CN,
$R^3$ is $C_{1-10}$ alkyl;
$R^4$ is hydrogen or $C_{1-10}$ alkyl;
$R^5$ is hydrogen or $C_{1-10}$ alkyl;
which process comprises reacting a substantially optically pure compound of formula (II),

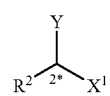

(II)

wherein
$R^2$ is as defined here above for compound of formula (I),
$X^1$ is as defined here above for X in compound of formula (I), and
Y is a leaving group selected from halogen, sulfonate group or —$N_2^+$,
with a substantially optically pure compound of formula (III), or salts thereof,

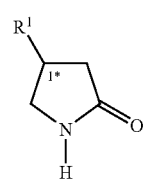

(III)

wherein $R^1$ is as defined here above for compound of formula (I).

Particular embodiments for R, X and Y groups are as defined here above for first aspect of the present invention.

Preferably, when $R^1$ is n-propyl, at least 95%, preferably at least 96%, more preferably at least 97%, most preferably at least 98%, even most preferably at least 99% of the compound of formula (III) has the stereogenic center indicated by (1*) in configuration (R).

Preferably, when $R^1$ is 2,2-difluorovinyl, at least 95%, preferably at least 96%, more preferably at least 97%, most preferably at least 98%, even most preferably at least 99% of the compound of formula (III) has the stereogenic center indicated by (1*) in configuration (S).

Preferably, at least 95%, preferably at least 96%, more preferably at least 97%, most preferably at least 98%, even most preferably at least 99% of compound of formula (I) has the stereogenic center indicated by (2*) in configuration (S).

In a particular embodiment according to the present invention, when $R^1$ is n-propyl, at least 95%, preferably at least 96%, more preferably at least 97%, most preferably at least 98%, even most preferably at least 99% of the compound of formula (III) has the stereogenic center indicated by (1*) in configuration (R) and at least 95%, preferably at least 96%, more preferably at least 97%, most preferably at least 98%, even most preferably at least 99% of the compound of formula (III) has the stereogenic center indicated by (2*) in configuration (S).

In another particular embodiment according to the present invention, when $R^1$ is 2,2-difluorovinyl, at least 95%, preferably at least 96%, more preferably at least 97%, most preferably at least 98%, even most preferably at least 99% of the compound of formula (III) has the stereogenic center indicated by (1*) in configuration (S) and at least 95%, preferably at least 96%, more preferably at least 97%, most preferably at least 98%, even most preferably at least 99% of the compound of formula (III) has the stereogenic center indicated by (2*) in configuration (S).

Compounds of formula (III) may be available commercially or may be synthesized according to methods described in Kenda et al., in J. Med. Chem. 2004, 47, 530-549.

Substantially optically pure compounds of formula (III) may be synthesized according to methods described in European patent applications n°05020080.7 and n°05023133.1 or according to any conventional methods known to the man skilled in the art.

Examples of compounds of formula (III) according to the present invention are pyrrolidin-2-one, 4-propylpyrrolidin-2-one, (R)-4-propylpyrrolidin-2-one, 4-(2,2-difluorovinyl)pyrrolidin-2-one, (S)-4-(2,2-difluorovinyl)pyrrolidin-2-one.

In a second aspect, the present invention relates to a process for the preparation of a compound of formula (I),

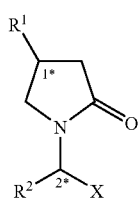

(I)

wherein,
$R^1$ is $C_{1-10}$ alkyl or $C_{2-6}$ alkenyl
$R^2$ is $C_{1-10}$ alkyl or $C_{2-6}$ alkenyl,
X is —CONR⁴R⁵, —COOH, —COOR³ or —CN,
$R^3$ is $C_{1-10}$ alkyl;
$R^4$ is hydrogen or $C_{1-10}$ alkyl;
$R^5$ is hydrogen or $C_{1-10}$ alkyl;

which process comprises reacting a substantially optically pure compound of formula (II),

(II)

wherein
$R^2$ is as defined here above for compound of formula (I),
$X^1$ is as defined here above for X in compound of formula (I), and
Y is a leaving group selected from halogen, sulfonate group or —N₂⁺, with a compound of formula (IV), or salts thereof,

(IV)

wherein
$R^2$ is as defined here above for compound of formula (I), and
$X^2$ is as defined here above for X in compound of formula (I).

In one embodiment according to second aspect of the present invention, $R^1$ is hydrogen, $C_{1-4}$ alkyl or $C_{2-4}$ alkenyl. In another embodiment according to second aspect of the present invention, $R^1$ is hydrogen, n-propyl or diflurorovinyl.

In one embodiment according to second aspect of the present invention, $R^2$ is $C_{1-4}$ alkyl. In another embodiment according to second aspect of the present invention, $R^2$ is ethyl.

In one embodiment according to second aspect of the present invention, X is —CONR⁴R⁵, —COOH or —COOR³, wherein $R^3$ is a $C_{1-4}$ alkyl. In another embodiment according to second aspect of the present invention, X is —CONR⁴R⁵.

In one embodiment according to second aspect of the present invention, $X^1$ is —CONR⁴R⁵ or —COOR³, wherein $R^3$ is a $C_{1-4}$ alkyl. In another embodiment according to second aspect of the present invention, $X^1$ is COOR³, wherein $R^3$ is a $C_{1-4}$ alkyl.

In one embodiment according to second aspect of the present invention, $X^2$ is —CONR⁴R⁵ or —COOR³, wherein $R^3$ is a $C_{1-4}$ alkyl. In another embodiment according to second aspect of the present invention, $X^2$ is COOR³, wherein $R^3$ is a $C_{1-4}$ alkyl.

In one embodiment according to second aspect of the present invention, $R^4$ is hydrogen or $C_{1-4}$ alkyl. In another embodiment according to second aspect of the present invention, $R^4$ is hydrogen.

In one embodiment according to second aspect of the present invention, $R^5$ is hydrogen or $C_{1-4}$ alkyl. In another embodiment according to second aspect of the present invention, $R^5$ is hydrogen.

In one embodiment according to second aspect of the present invention, Y is a halogen or a sulfonate group. In another embodiment according second aspect of the present invention, Y is bromine, a methanesulfonate or a trifluromethanesulfonate group.

In a particular embodiment according to the present invention, $R^1$ is hydrogen, n-propyl or 2,2-difluorovinyl; $R^2$ is ethyl; X is —CONH$_2$; X$^1$ or X$^2$ is —CONH$_2$, COOH or COOMe; and Y is bromine, methanesulfonate or trifluoromethanesulfonate.

In another embodiment according to the present invention, compound of formula (IV) is substantially optically pure.

In a particular embodiment, at least 95%, preferably at least 96%, more preferably at least 97%, most preferably at least 98%, even most preferably at least 99% of the compound of formula (IV) has the stereogenic center indicated by (3*) in configuration (S) when R$^1$ is 2,2-diflurovinyl.

In another particular embodiment, at least 95%, preferably at least 96%, more preferably at least 97%, most preferably at least 98%, even most preferably at least 99% of the compound of formula (IV) has the stereogenic center indicated by (3*) in configuration (R) when R$^1$ is n-propyl.

Examples of salts of compounds of formula (IV) are sulfate, acetate, trifluroacetate, hydrobromine or hydrochloride.

The reaction of compound (II) with compound (IV) generally occurs in the presence of a base.

Examples of bases which may be used in the process according to second aspect of the present invention are potassium hydride, sodium hydride, sodium methoxide, potassium methoxide, sodium isopropoxide, sodium tert-butoxide, potassium tert-butoxid, potassium carbonate, sodium carbonate, triethylamine, cesium carbonate, triisopropylamine (Hünig's base).

Examples of solvents which may be used in the process according to second aspect of the present invention are methanol, isopropanol, tert-butanol, dimethoxyethane, dimethylsulphoxide, dichloromethane, acetonitrile and toluene or mixtures thereof.

The processes according to the present invention are generally achieved at a temperature ranging from 0° C. to 100° C., preferably ranging from 0° C. to 70° C.

The reaction of compound of formula (II) with compound of formula (IV) generally affords compound of formula (VI), which compound may be further converted to compound of formula (I), for example by cyclisation, according to methods described in international patent application published under number WO 01/62726.

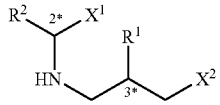

(VI)

For example, compound of formula (VI) may be reacted with or without a catalytic quantity of 2-hydroxy-pyridine in toluene at a temperature comprised between 50° C. and 100° C.

Thus in a particular embodiment, the process according to second aspect of the invention further comprises cyclisation of compound of formula (VI).

Thus, in a further aspect, the present invention relates to the use of compounds of formula (VI) for the synthesis of compounds of formula (I). Compound of formula (I), wherein X is —CO—NR$^4$R$^5$ may be obtained directly by reacting compound of formula (VI) wherein X$^1$ is —CO—NR$^4$R$^5$.

Compound of formula (VI) wherein X$^1$ is —CO—NR$^4$R$^5$ may be obtained by reacting compound of formula (II) wherein X$^1$ is —CO—NR$^4$R$^5$ with compound of formula (IV).

Alternatively, compound of formula (II) wherein X$^1$ is COOR$^3$ or COOH may be reacted with compound of formula (IV) to afford compound of formula (VI) wherein X$^1$ is COOR$^3$ or COOH which is subsequently converted to compound of formula (V) wherein X$^1$ is COOR$^3$ or COOH. Said compound of formula (V) is converted to compound of formula (I) as described here above in the specification.

R$^1$, R$^2$, X$^1$ and X$^2$ in compounds of formula (VI) are as defined for compounds of formula (II) and of formula (IV) in the above specification.

In a particular embodiment according to this aspect of the invention compounds of formula (VI), wherein R$^1$ is different from hydrogen, are diastereoisomerically enriched.

In another particular embodiment according to this aspect of the invention compounds of formula (VI), wherein R$^1$ is different from hydrogen, are substantially diastereoisomerically pure.

Thus, in a further particular embodiment, the present invention relates to the use of substantially diastereoisomerically pure compound of formula (VI), wherein R$^1$ is C$_{1-10}$ alkyl or C$_{2-6}$ alkenyl, R$^2$, R$^3$, R$^4$, R$^5$, X$^1$ and X$^2$ being as defined here above in the specification, for the synthesis of substantially diastereoisomerically pure compound of formula (I) wherein R$^1$ is C$_{1-10}$ alkyl or C$_{2-6}$ alkenyl, R$^2$, R$^3$, R$^4$, R$^5$ and X$^1$ being as defined here above in the specification.

In particular, substantially diastereosiomerically pure compounds of formula (VI) wherein R$^1$ is n-propyl may be used for the synthesis of brivaracetam.

Examples of substantially diastereoisomerically pure compounds of formula (VI) wherein R$^1$ is n-propyl are (R)-3-[((S)-1-carboxypropylamino)methyl]hexanoic acid, methyl-(R)-3-[((S)-1-carboxypropylamino)methyl]hexanoate, ethyl-(R)-3-[((S)-1-carboxypropylamino)methyl]hexanoate, (R)-3-[((S)-1-methoxycarbonylpropylamino)methyl]hexanoic acid, methyl-(R)-3-[((S)-1-methoxycarbonylpropylamino)methyl]hexanoate, ethyl-(R)-3-[((S)-1-methoxycarbonylpropylamino)methyl]hexanoate, (R)-3-[((S)-1-carbamoylpropylamino)methyl]hexanoic acid, methyl-(R)-3-[((S)-1-carbamoylpropylamino)methyl]hexanoate, ethyl-(R)-3-[((S)-1-carbamoylpropylamino)methyl]hexanoate.

In particular, substantially diastereoisomerically pure compounds of formula (VI) wherein R$^1$ is 2,2-difluorovinyl may be used for the synthesis of seletracetam.

Examples of substantially diastereoisomeric ally pure compounds of formula (VI) wherein R$^1$ is 2,2-difluorovinyl are (S)-3-[((S)-1-carboxypropylamino)methyl]-5,5-difluoropent-4-enoic acid, methyl-(S)-3-[((S)-1-carboxypropylamino)methyl]-5,5-difluoropent-4-enoate, ethyl-(S)-3-[((S)-1-carboxypropylamino)methyl]-5,5-difluoropent-4-enoate, (S)-3-[((S)-1-methoxycarbonylpropylamino)methyl]-5,5-difluoropent-4-enoic acid, methyl-(S)-3-[((S)-1-methoxycarbonylpropylamino)methyl]-5,5-difluoropent-4-enoate, ethyl-(S)-3-[((S)-1-methoxycarbonylpropylamino)methyl]-5,5-difluoropent-4-enoate, (R)-3-[((S)-1-carbamoylpropylamino)methyl]-5,5-difluoropent-4-enoic, methyl-(R)-3-[((S)-1-carbamoylpropylamino)methyl]-5,5-difluoropent-4-enoate, ethyl-(R)-3-[((S)-1-carbamoylpropylamino)methyl]-5,5-difluoropent-4-enoate 4-[(S)-1-carboxypropylamino]butyric acid.

Substantially optically pure compounds of formula (II) are commercially available or alternatively may be synthesized, for example by chemical resolution or by enantioselective synthesis, according to any of the methods described in the following references : Bottini & al., J. Org. Chem., 1963, 28, 156-158 ; Bellucci & al., Tetrahedron, 1969, 25(18), 4167-4172 ; Compagnone & al., J. Org. Chem., 1986, 51, 1713-1719; Chenault & al., J. Org. Chem., 1987, 52(12), 2608-

2611; Hoekstra & al., Org. Process research & Developement, 1997, 1, 26-38; Lee, Tetrahedron, 1967, 23, 359-363; Ferorelli, Il Farmaco, 1997, 52(6-7), 367-374; Boyes, J. Chem. Soc. Perkin Trans I, 2000, 2759-2765

Compounds of formula (IV) are commercially available or alternatively are synthesized according to any conventional method known to the person skilled in the art and for example, by ring opening of the corresponding pyrrolidone derivative by treatment with an aqueous or alcoholic acid solution or according to the method described in Kenda et al., in J. Med. Chem. 2004, 47, 530-549.

Examples of compounds of formula (IV) according to the present invention are 4-aminobutyric acid, methyl-4-aminobutyrate, ethyl-4-aminobutyrate, (R)-3-propyl-4-aminobutyric acid, methyl-(R)-3-propyl-4-aminobutyrate, ethyl-(R)-3-propyl-4-aminobutyrate, (S)-3-(2,2-difluorovinyl)-4-aminobutyric acid, methyl-(S)-3-(2,2-difluorovinyl)-4-aminobutyrate, and ethyl-(S)-3-(2,2-difluorovinyl)-4-aminobutyrate.

Compounds of formula (II) wherein Y is $-N_2^+$ may be generated in situ from the corresponding amino group, by reaction with $NaNO_2$ in the presence of an acid according to methods described, for example, in the following references: J. Chem. Soc. Chem. Commun. 1976, 234; J. Am. Chem. Soc. 1949, 71, 1096; J. Am. Chem. Soc. 1990, 112(17), 6388; Helv. Chem. Acta, 1963, 46, 927 or according to any conventional methods known to the person skilled in the art.

Examples of compounds of formula (II) according to the present invention are (R)-2-bromobutyric acid, methyl-(R)-2-bromobutyrate, ethyl-(R)-2-bromobutyrate, (R)-2-bromobutyramide, (R)-2-methanesulfonyloxybutyric acid, methyl-(R)-2-methanesulfonyloxybutyrate, ethyl-(R)-2-methanesulfonyloxybutyrate, methanesulfonic acid (R)-1-carbamoyl-propyl ester, (R)-2-p-toluenesulfonyloxybutyric acid, methyl-(R)-2-p-toluenesulfonyloxybutyrate, ethyl-(R)-2-p-toluenesulfonyloxybutyrate, p-tolueneesulfonic acid (R)-1-carbamoyl-propyl ester, (R)-1-carboxy-propanediazonium, (R)-1-methoxycarbonyl-propanediazonium, (R)-1-ethoxycarbonyl-propanediazonium, (R)-1-carbamoyl-propanediazonium, (R)-2-bromopropionic acid, methyl-(R)-2-bromopropionate, ethyl-(R)-2-bromopropionate, (R)-2-bromopropionamide, (R)-2-methanesulfonyloxybutyric acid, methyl-(R)-2-methanesulfonyloxypropionate, ethyl-(R)-2-methanesulfonyloxypropionate, methanesulfonic acid (R)-1-carbamoyl-ethyl ester, (R)-2-p-toluenesulfonyloxypropionic acid, methyl-(R)-2-p-toluenesulfonyloxypropionate, ethyl-(R)-2-p-toluenesulfonyloxypropionate, p-toluenesulfonic acid (R)-1-carbamoyl-ethyl ester, (R)-1-carboxy-ethanediazonium, (R)-1-methoxycarbonyl-ethanediazonium, (R)-1-ethoxycarbonyl-ethanediazonium, (R)-1-carbamoyl-ethanediazonium, (R)-2-trifluoromethanesulfonyloxybutyric acid, methyl-(R)-2-trifluoromethanesulfonyloxybutyrate, ethyl-(R)-2-trifluoromethanesulfonyloxybutyrate, and trifluoromethanesulfonic acid (R)-1-carbamoyl-propyl ester.

The process according to the present invention may optionally comprise a step of separation of the different diastereoisomers, particularly a step of separation of one or more of the different diastereoisomers of any of the compounds of formula (I), (IV), (V) or (VI). Said separation may be achieved by liquid column chromatography or by recrystalllisation according to conventional methods known to the person skilled in the art.

In a further particular embodiment, the present invention relates to a process for the preparation of levetiracetam,

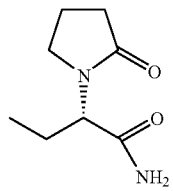

which process comprises reacting a substantially optically pure compound of formula (IIa), (IIa)
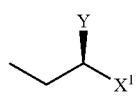

wherein
$X^1$ is $-CONR^4R^5$, $-COOH$, or $-COOR^3$;
$R^3$ is $C_{1-4}$ alkyl;
$R^4$ is hydrogen or $C_{1-4}$ alkyl;
$R^5$ is hydrogen or $C_{1-4}$ alkyl;
Y is a leaving group selected from halogen, sulfonate group or $-N_2^+$ with pyrrolidine-2-one.

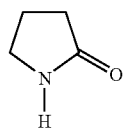

In another further particular embodiment, the present invention relates to a process for the preparation of brivaracetam,

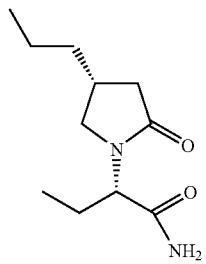

which process comprises reacting a substantially optically pure compound of formula (IIa), (IIa)
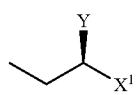

wherein
$X^1$ is $-CONR^4R^5$, $-COOH$ or $-COOR^3$
$R^3$ is $C_{1-4}$ alkyl;
$R^4$ is hydrogen or $C_{1-4}$ alkyl;

$R^5$ is hydrogen or $C_{1-4}$ alkyl;

Y is a leaving group selected from halogen, sulfonate group or $-N_2^+$ with a compound of formula (IIIa), or salts thereof,

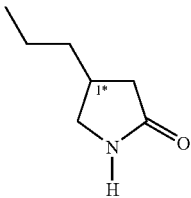
(IIIa)

In one embodiment, $X^1$ is $CONR^4R^5$ or $-COOR^3$. In another embodiment $X^1$ is $CONR^4R^5$. In a further embodiment $X^1$ is $-CONH_2$.

In one embodiment Y is halogen or sulfonate group. In another embodiment Y is bromine, a methanesulfonate or a trifluromethanesulfonate group.

In one embodiment, compound of formula (IIIa) is substantially optically pure (R)-4-propyl-pyrrolidin-2-one.

In another further particular embodiment, the present invention relates to a process for the preparation of seletracetam,

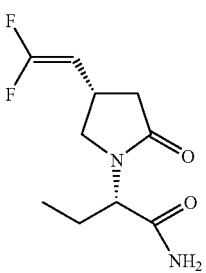

which process comprises reacting a substantially optically pure compound of formula (IIa),

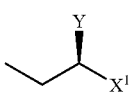
(IIa)

wherein
$X^1$ is $-CONR^4R^5$, $-COOH$ or $-COOR^3$,
$R^3$ is $C_{1-4}$ alkyl;
$R^4$ is hydrogen or $C_{1-4}$ alkyl;
$R^5$ is hydrogen or $C_{1-4}$ alkyl;
Y is a leaving group selected from halogen, sulfonate group or $-N_2^+$
with a compound of formula (IIIb), or salts thereof,

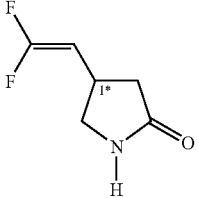
(IIIb)

In one embodiment, $X^1$ is $CONR^4R^5$ or $-COOR^3$. In another embodiment $X^1$ is $CONR^4R^5$. In a further embodiment $X^1$ is $-CONH_2$.

In one embodiment, Y is halogen or sulfonate group. In another embodiment Y is bromine, a methanesulfonate or a trifluromethanesulfonate group.

In one embodiment, compound of formula (IIIb) is substantially optically pure (S)-4-(2,2-difluoro-vinyl)-pyrrolidin-2-one.

In a particular embodiment, the present invention relates to a process for the preparation of levetiracetam,

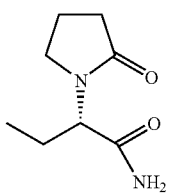

which process comprises reacting a substantially optically pure compound of formula (IIa),

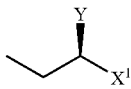
(IIa)

wherein
$X^1$ is $-CONR^4R^5$, $-COOH$ or $-COOR^3$;
$R^3$ is $C_{1-4}$ alkyl;
$R^4$ is hydrogen or $C_{1-4}$ alkyl;
$R^5$ is hydrogen or $C_{1-4}$ alkyl;
Y is a leaving group selected from halogen, sulfonate group or $-N_2^+$
with a compound of formula (IV'), or salts thereof,

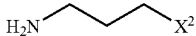
(IV')

wherein,
$X^2$ is $-CONR^4R^5$, $-COOH$, $-COOR^3$ or $-CN$,
$R^3$ is $C_{1-4}$ alkyl;
$R^4$ is hydrogen or $C_{1-4}$ alkyl;
$R^5$ is hydrogen or $C_{1-4}$ alkyl.

In a further particular embodiment, the present invention relates to a process for the preparation of brivaracetam,

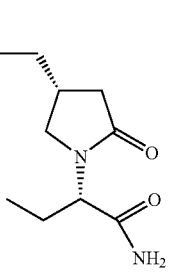

which process comprises reacting a substantially optically pure compound of formula (IIa),

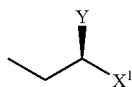
(IIa)

wherein
$X^1$ is —CONR$^4$R$^5$, —COOH, —COOR$^3$,
$R^3$ is C$_{1-4}$ alkyl;
$R^4$ is hydrogen or C$_{1-4}$ alkyl;
$R^5$ is hydrogen or C$_{1-4}$ alkyl;
Y is a leaving group selected from halogen, sulfonate group or —N$_2^+$
with a compound of formula (IVa), or salts thereof,

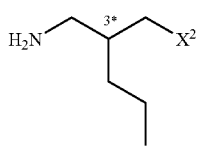
(IVa)

wherein,
$X^2$ is —CONR$^4$R$^5$, —COOH, —COOR$^3$ or —CN,
$R^3$ is C$_{1-4}$ alkyl;
$R^4$ is hydrogen or C$_{1-4}$ alkyl;
$R^5$ is hydrogen or C$_{1-4}$ alkyl.

In one embodiment, $X^1$ is CONR$^4$R$^5$ or —COOR3. In another embodiment $X^1$ is CONR4R5. In a further embodiment $X^1$ is —CONH$_2$.

In one embodiment, Y is halogen or sulfonate group. In another embodiment Y is bromine, a methanesulfonate or a trifluromethanesulfonate group.

In one embodiment, $X^2$ is CONR$^4$R$^5$ or —COOR$^3$. In another embodiment $X^2$ is —COOR$^3$.

In another embodiment, the present invention relates to a process for the preparation of seletracetam,

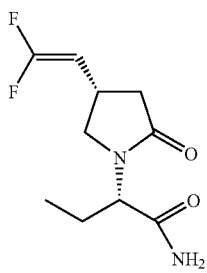

which process comprises reacting a substantially optically pure compound of formula (IIa),

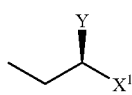
(IIa)

wherein
$X^1$ is —CONR$^4$R$^5$, —COOH, —COOR$^3$,
$R^3$ is C$_{1-4}$ alkyl;
$R^4$ is hydrogen or C$_{1-4}$ alkyl;
$R^5$ is hydrogen or C$_{1-4}$ alkyl;
Y is a leaving group selected from halogen, sulfonate group or —N$_2^+$
with a compound of formula (IVb), or salts thereof,

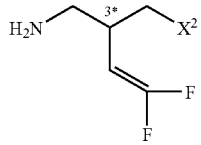
(IVb)

wherein,
$X^2$ is —CONR$^4$R$^5$, —COOH, —COOR$^3$ or —CN,
$R^3$ is C$_{1-4}$ alkyl;
$R^4$ is hydrogen or C$_{1-4}$ alkyl;
$R^5$ is hydrogen or C$_{1-4}$ alkyl.

In one embodiment, $X^1$ is CONR$^4$R$^5$ or —COOR$^3$. In another embodiment $X^1$ is CONR$^4$R$^5$. In a further embodiment $X^1$ is -CONH$_2$.

In one embodiment, Y is halogen or sulfonate group. In another embodiment Y is bromine, a methanesulfonate or a trifluromethanesulfonate group.

In one embodiment, $X^2$ is CONR$^4$R$^5$ or —COOR$^3$. In another embodiment $X^2$ is —COOR$^3$.

In a particular embodiment according to the present invention, compound of formula (IVa) and compound of formula (IVb) are substantially optically pure. In a further particular embodiment, at least 95%, preferably at least 96%, more preferably at least 97%, most preferably at least 98%, even most preferably at least 99% of compound of formula (IVa) has the stereogenic center indicated by (3*) in configuration (R) and compound of formula (IVb) has the stereogenic center indicated by (3*) in configuration (S).

EXAMPLES

The following examples are provided for illustrative purposes only and are not intended, nor should they be construed, as limiting the invention in any manner. Those skilled in the art will appreciate that routine variations and modifications of the following examples can be made without exceeding the spirit or scope of the invention.

Characterization of compounds of the following examples is achieved using the following techniques and conditions:

NMR spectra are recorded on a Bruker 400 MHz Spectrometer. The compound is studied in DMSO-d6 (or CDCl3) solution at a probe temperature of 313 K or 300 K and at a concentration of 15 mg/ml. The instrument is locked on the deuterium signal of DMSO-d6 (or CDCl3). Chemical shifts are given in ppm downfield from TMS taken as internal standard.

Gas chromatography spectra are recorded on a Thermo Finnigan Trace-2000 system equipped with an Altech GC DB-1701 (15 m×0.25mm i.d.×0.25 µm film thickness) column. Dihydrogen is used as carrier gas in a constant flow of 1.5 ml/min. Sample (1 µl) is injected in a split/splitlesss mode (injector, 250° C., hot-needle injection with CTC Combi-PAL autosampler) and the oven temperature is programmed as follows: increasing from 50° C. to 280° C. (15.3° C./min.) and holding for 20 min. The detector temperature (FID-AUX) is set at 300° C.

Chiral High Performance Liquid Chromatograpy (HPLC) analyses are performed using one of the following systems:
a TSP-system mounted with a Chiralpak AD-H, 250×4.6 mm, 5.0 µm column. Eluent is a constant mixture of n-Hexane/Ethanol/Trifluoroacetic acid (96/3.9/0.1) and the flow rate is set at 1.5 ml/min. The run time is of 30 min. and the chromatography is carried out at 25° C.

a TSP-system mounted with a Chiralpak AD-H, 250×4.6 mm, 5.0 μm column. Eluent is a constant mixture of 67% solvent A (0.1% diethylamine in n-Heptane) and 33% solvent B (0.1% diethylamine in Ethanol). The flow rate is set at 1.0 ml/min and the temperature of the column is set at 25° C.

Example 1

Synthesis of Substantially Optically Pure methyl-(S)-2-(2-oxopyrrolidin-1-yl)butyrate (Ia) (Compound (I) with $R^1$=H, $R^2$=Et, X=COOMe)

1a. Synthesis of methyl-(R)-2-trifluoromethanesulfonyloxybutyrate (IIc) (compound (II) with $R^2$=Et, $X^1$=COOMe, Y=OTf)

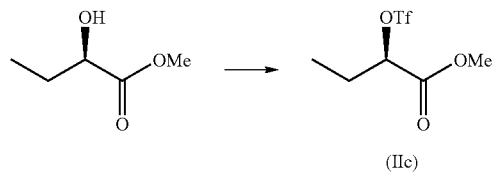

(IIc)

A mixture of methyl-(R)-2-hydroxybutyrate (5.0 g, 42.3 mmol) and pyridine (3.7 g, 46.8 mmol, 1.1 equiv.) in dichloromethane (25 ml, 5 vol.) is added dropwise over a period of 30 min. to a solution of triflic anhydride (13.13 g, 46.5 mmol, 1.1 equiv.) in dichloromethane (50 ml, 10 vol.) cooled to 0-5° C. The mixture is then warmed to 20° C. and water (50 ml, 10 vol.) is added. Aqueous and organic layers are separated and the organic layer is washed with 50 ml of water. After drying over sodium sulfate (4.0 g) the organic layer is concentrated under reduced pressure to afford pure methyl-(R)-2-trifluoromethanesulfonyloxybutyrate as yellow oil (10.0 g, 39.9 mmol, 94%).

GC: retention time=3.39 min. (100%)

1H NMR δH (400 mHz, CDCl3): 1.07 (3H, t, J 7.5), 2.0-2.12 (2H, m), 3.86 (3H, s), 5.10 (1H, dd, J7.7; 5.0)

1.b. Synthesis of methyl-(S)-2-(2-oxopyrrolidin-1-yl)butyrate(Ia)

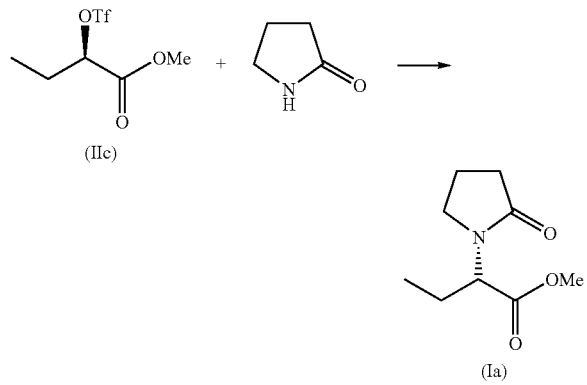

A mixture of pyrrolidone (1.36 g, 16 mmol) and 30% sodium methoxide in methanol (3 ml, 16 mmol, 1 equiv.) is heated in toluene to 80° C. and then concentrated under reduced pressure to half volume of toluene. The residue is cooled to 0° C. and compound (IIa) is added dropwise. The mixture is stirred at room temperature.

After 4 days, 50 ml of water is added and the two resulting layers are separated and the aqueous phase extracted with 50 ml of toluene. The combined organic layers are washed with 50 ml of water and then concentrated under reduced pressure to afford methyl-(S)-2-(2-oxopyrrolidin-1-yl)butyrate (2.2 g, 11.9 mmol, 74%).

GC: retention time=7.89 min. (95.8%)

Chiral HPLC: 89.26% (S)/10.74% (R)

Example 2

Synthesis of levetiracetam

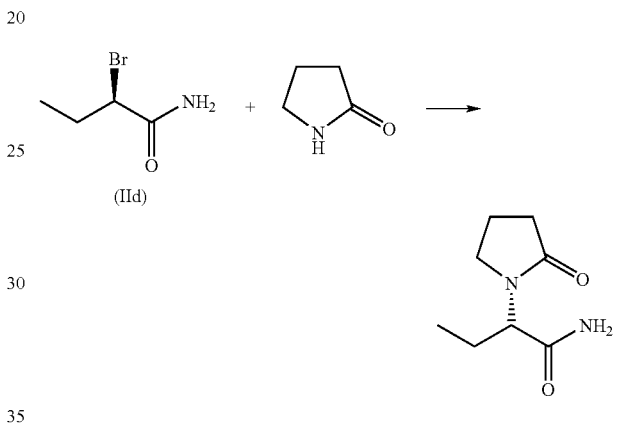

To a solution of pyrrolidine-2-one (85 mg, 1 mmol) in 6 ml of toluene is added sodium methoxide (0. 19 ml of a 30% solution in MeOH, 1 mmol, 1 equiv.). The mixture is heated to 40° C. and concentrated to dryness under reduced pressure. The solid residue is taken up in 3 ml of tetrahydrofuran, cooled to 0° C. and (R)-2-bromobutyramide (IId) (optical purity >98%) (166 mg, 1 mmol, 1 equiv.) is added. The mixture is stirred for 1 h at 0° C. and further 16 h at room temperature. The mixture is then concentrated to dryness under reduce pressure.

GC: 40.3% conversion

Chiral HPLC: 51.0% (S)/49.0% (R)

Example 3

Synthesis of (S)-2-[(S)-4-(2,2-difluoro-vinyl)-2-oxopyrrolidin-1-yl]butyric acid (Ib) (Compound (I) with $R^1$=2,2-difluorovinyl, $R^2$=Et, X=COOH)

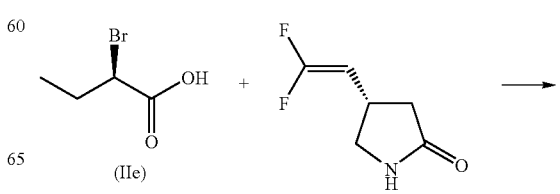

(IIe)

-continued

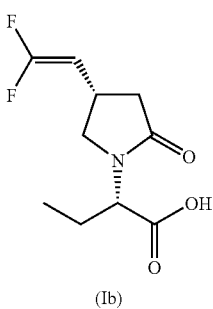

(Ib)

To a suspension of substantially optically pure (S)-4-(2,2-difluorovinyl)pyrrolidon-2-one (0.59 g, 4.0 mmol, 2 equiv.) in tetrahydrofuran (5 ml, 12 vol.) at room temperature is added sodium hydride (60% oily dispersion, 0.16 g, 4.0 mmol, 2 equiv.). The mixture is stirred for 1 hour and (R)-2-bromobutyric acid (IIe) (0.33 g, 2 mmol, 1 equiv.) in tetrahydrofuran (2 ml) is added. The mixture is stirred until complete conversion. After 48 hours, 10% aqueous HCl (2 ml) is added and the two layers are separated. Aqueous layer is extracted with dichloromethane (20 ml). Organic layers are combined, dried over magnesium sulfate and concentrated to dryness under reduced pressure to yield (S)-2-[(S)-4-(2,2-difluorovinyl)-2-oxopyrrolidin-1-yl]butyric acid (0.19 g, 0.8 mmol, 41%).

1H NMR δH of (Ib) (400 mHz, CDCl3): 0.95 (3H, t, J 7.5), 1.65-1.77 (1H, m), 2.02-2.13 (1H, m), 2.31 (1H, dd, J16.8; 8.0), 2.72 (1H, dd, J16.8; 8.0), 3.12-3.22 (1H, m), 3.32 (1H, t, J8.2), 3.53 (1H, t, J8.2), 4.35 (1H, ddd, J24.5; 9.5; 1.4), 4.67 (1H, dd, J10.8; 4.9), 8.26 (1H, brs).

Example 4

Synthesis of (S)-2-[4-propyl-2-oxopyrrolidin-1-yl]butyri acids (Ix) (Compound (I) with $R^1$=n-propyl, $R^2$=Et, X=COOH)

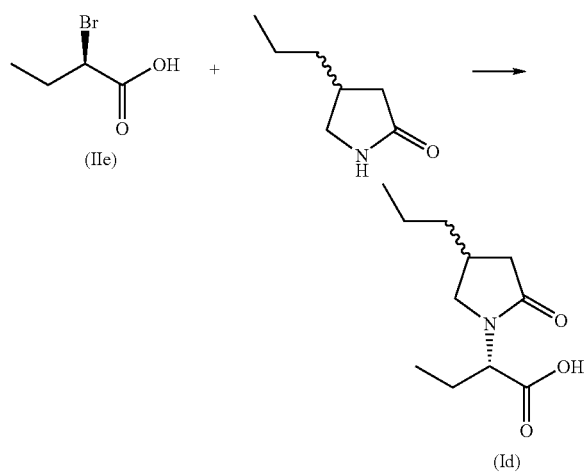

(Id)

To a suspension of NaH (60% oily dispersion, 0.32 g, 8.0 mmol, 4 equiv.) previousely washed twice with heptane was added a solution racemic 4-propyl-pyrrolidon-2-one (0.76 g, 6.0 mmol, 3 equiv.) in tetrahydrofuran (5 ml). The mixture was stirred until end of gas evolution and (R)-2-bromobutyric acid (0.33 g, 2.0 mmol, 1 equiv.) in tetrahydrofuran (5 ml) is added at room temperature. The mixture was stirred overnight. Aqueous 1M NaOH solution (15 ml) was added and the resulting two layers separated. The aqueous phase was washed with dichloromethane (3×15ml) and then acidified with a 1N HCl solution (to pH=2). The resulting acidic aqueous phase was extracted twice with ethyl acetate (2×15 ml). The combined organic phases were dried (MgSO4), filtered and concentrated to dryness under reduced pressure yielding diastereomeric mixture of (S)-2-[4-propyl-2-oxopyrrolidin-1-yl]butyric acid (0.26 g, 1.2 mmol, 60%)

Chiral HPLC: 90.3% (S,S and R,S not baseline separated)/ 4.0% (S,R)/5.7% (R,R)

Example 5

Synthesis of Substantially Optically Pure (S)-2-[(S)-4-propyl-2-oxopyrrolidin-1-yl]butyric Acid (Ic) (Compound (I) with $R^1$=n-propyl $R^2$=Et X —COOH)

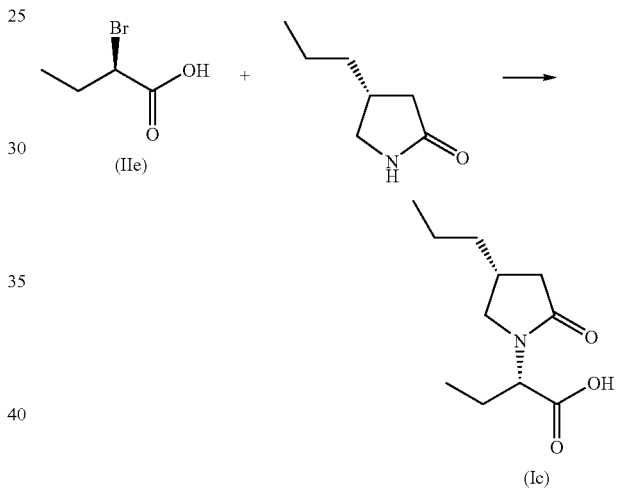

(Ic)

To a suspension of NaH (60% oily dispersion, 0.96 g, 24.0 mmol, 4 equiv.) previousely washed twice with heptane was added a solution of substantially optically pure (S)-4-propyl-pyrrolidon-2-one (2.30 g, 18.0 mmol, 3 equiv.) in tetrahydrofuran (10 ml, 4.5 vol.). The mixture was stirred until end of gas evolution and (R)-2-bromobutyric acid (1.00 g, 6 mmol, 1 equiv.) in tetrahydrofuran (10 ml) is added at room temperature. The mixture was stirred overnight. Aqueous 1M NaOH solution (15 ml) was added and the resulting two layers separated. The aqueous phase was washed with dichloromethane (3×15ml) and then acidified with a 1N HCl solution (16 ml). The resulting acidic aqueous phase was extracted twice with ethyl acetate (2×40 ml). The combined organic phases were dried (MgSO4), filtered and concentrated to dryness under reduced pressure yielding (S)-2-[(S)-4-propyl-2-oxopyrrolidin-1-yl]butyric acid (0.97 g, 4.6 mmol, 77%)

Chiral HPLC: 95.9% (S,S)/4.1% (S,R)

1H NMR δH of (Ic) (400 mHz, CDCl3): $^1$H NMR $δ_H$ (400 mHz, CDCl$_3$): 0.91-0.95 (6H, m), 1.29-1.39 (2H, m), 1.42-1.50 (2H, m), 1.65-1.77 (1H, m), 2.00-2.11 (1H, m), 2.17 (1H, dd, J16.7; 8.2), 2.28-2.40 (1H, m), 2.60 (1H, dd, J16.7; 8.2), 3.18 (1H, dd, J9.3; 7.2), 3.43 (1H, dd, J9.4; 7.9), 4.63 (1H, dd, J10.7; 5.0), 9.01 (1H, brs)

Example 6

Synthesis of Substantially Optically Pure methyl-(S)-2-(2-oxopyrrolidin-1-yl)butyrate (Ia) (compound (I) with R¹=H, R²=Et, X=COOMe)

6.1. Synthesis of substantially optically pure methyl-(S)-2-(2-oxopyrrolidin-1-yl)butyrate (Ia)

6.1.1. Synthesis of methyl-4-(1-methoxycarbonylpropylamino)butyrate (VIa)(compound (VI) where R¹=H, X¹=COOMe, R²=Et, X²=COOMe)

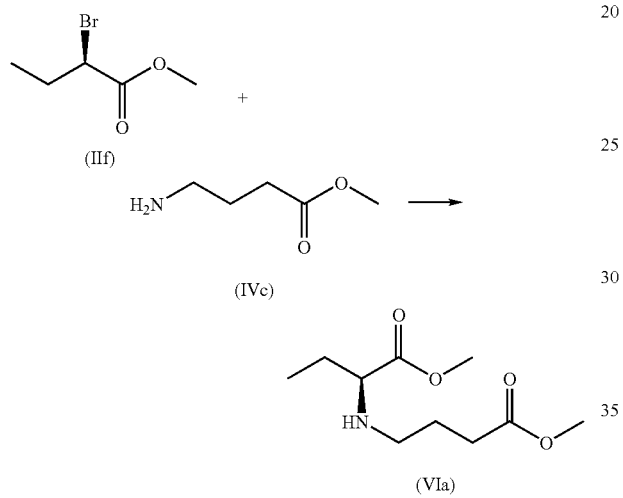

To a mixture of potassium carbonate (19 g, 138 mmol, 5 equiv.) and methyl-4-aminobutyrate (IVc) (8.5 g, 55.3 mmol, 2 equiv.) in acetonitrile (70 ml, 14 vol.) is added methyl-(R)-2-bromobutyrate (IIf) (5 g, 27.6 mmol, 1 equiv.). The suspension is stirred at 40° C. for 19 hours. The mixture is then filtered and the cake is rinsed with 50 ml of acetonitrile. The filtrate is concentrated to dryness under reduced pressure and the residue is dissolved in isopropylactetate. The resulting organic layer is washed with 60 ml of water and is concentrated under vacuum to afford methyl-4-(1-methoxycarbonylpropylamino)butyrate (VIa) as a colourless oil (5.91 g, 27.2 mmol, 98%).

GC: retention time=7.07 min (>99%)

6.1.2. Synthesis of (methyl-(S)-2-(2-oxopyrrolidin-1-yl)butyrate (Ia) (Compound (I) with R¹=H. R²=Et, X=COOMe)

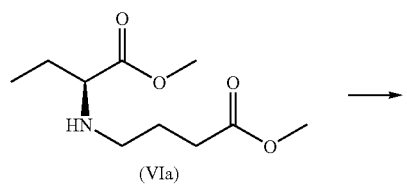

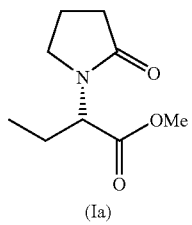

Compound (VIa) (5.8 g, 26.7 mmol) is dissolved in 50 ml of toluene. 2-hydroxy-pyridine (350 mg, 3.7 mmol, 14 mol %) is added and the mixture is stirred at 80° C. for 17 hours. The mixture is cooled to room temperature and 40 ml of water is added. The water layer is separated from organic phase and extracted from 40 ml of isopropylacetate. The combined organic layers are concentrated to dryness to afford (S)-2-(2-oxopyrrolidin-1-yl)butyric acid methyl ester (Ia) (4.4 g, 23.7 mmol, 89%)

GC: retention time=7.89 min

Chiral HPLC: 70.5% (S)/29.5% (R)

1H NMR δH (400 mHz, CDCl3): 0.92 (3H, t, J 7.4), 1.65-1.73 (1H, m), 1.99-2.12 (3H, m), 2.44 (2H, t, J8.0), 3.32-3.37 (1H, m), 3.49-3.55 (1H, m), 3.71 (3H, s), 4.69 (1H, dd, J7.9, 5.2)

6.2. Synthesis of methyl-(S)-2-(2-oxopyrrolidin-1-yl)butyrate (Ia) (compound (I) with R¹=H, R²=Et, X=COOMe) starting from (IIg)

6.2.1. Synthesis of methyl-(R)-2-methanesulfonyloxybutyrate (IIg) (compound (II) with R²=Et, X¹=COOMe, Y=OMes)

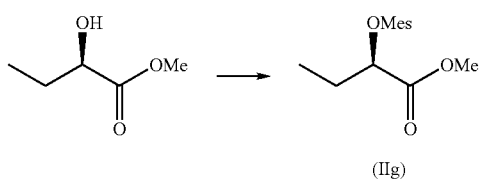

To a solution of methanesulfonic acid chloride (5.33 g, 46.5 mmol, 1.1 equiv.) in dichloromethane (50 ml, 11 vol.) cooled to 0-5° C. is added over a period of 30 min. a mixture of methyl-(R)-2-hydroxybutyrate (5.1 g, 43.2 mmol, 1 equiv.) and triethylamine (4.7 g, 46.5 mmol, 1.1 equiv.) in dichloromethane (25 ml). When conversion is complete (TLC: methylcyclohexane/ethyl acetate=1/1 (v/v), dying with molybdatophosphoric acid; Rf=0.5), the mixture is allowed to warm to room temperature and 50 ml of water is added. The two resulting layers are separated and the organic layer is washed with 50 ml of water. The organic layer is dried over sodium carbonate and concentrated under reduced pressure to afford methyl-(R)-2-methanesulfonyloxybutyrate (IIg) as yellow oil (8.5 g, 43.2 mmol, 100%)

1H NMR δH (400 mHz, CDCl3): 1.04 (3H, t, J 7.4), 1.89-2.03 (2H, m), 3.16 (3H, s), 3.81 (3H, s), 5.00 (1H, dd, J7.6; 4.6)

6.2.2. Synthesis of ethyl-(S)-4-[(1-methoxycarbonyl)propylamino]butyrate (VIb) (compound (VI) with $R^1$=H, $X^1$=COOMe, $R^2$=Et, $X^2$=COOEt)

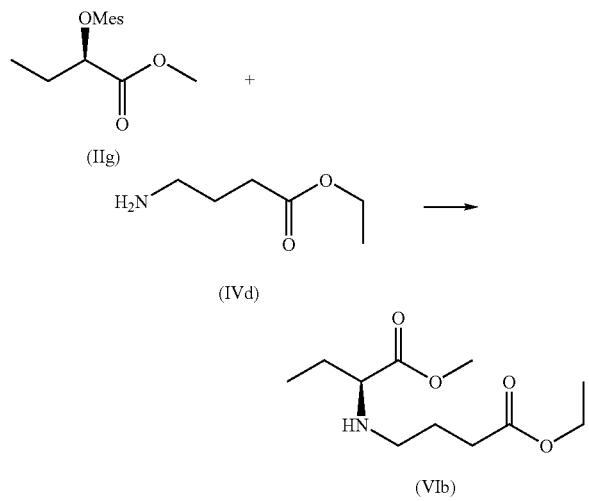

A mixture of methyl-(R)-2-methanesulfonyloxybutyrate (IIg) (4.0 g, 20.4 mmol, 1 equiv.), ethyl-4-aminobutyrate (IVb) (8.0 g, 61.0 mmol, 3 equiv.) in dimethylsulfoxyde (40 ml, 10 vol.) is heated at 70° C. for 40 hours. The mixture is cooled to 20° C. and water (40 ml) and isopropyl acetate (100 ml) are added successively. The two layers are separated and the aqueous layer is extracted with isopropyl acetate (50 ml). The combined organic layers are washed with water (20 ml) and concentrated under reduced pressure to afford ethyl-(S)-4-[(1-methoxycarbonyl)propylamino]butyrate (VIb) as a yellow oil. (3.6 g, 15.5 mmol, 76.3%)

GC: retention time=2.88 min (>97%)

6.2.3. Synthesis of (S)-2-(2-oxopyrrolidin-1-yl)butyric acid methyl ester (Ia)

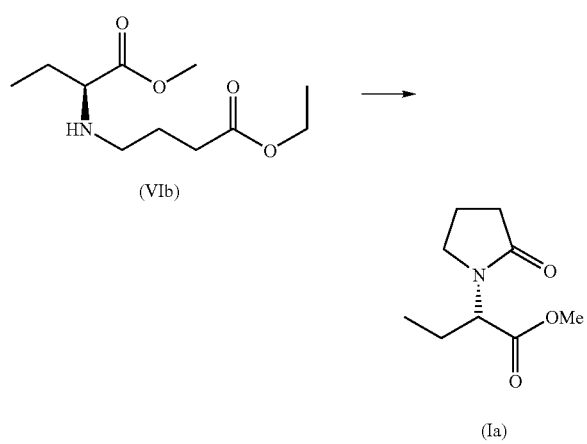

A mixture of crude ethyl-(S)-4-[(1-methoxycarbonyl)propylamino]butyrate (VIb) (1.0 g, 4.3 mmol) and 2-hydroxy pyrridine (0.12 g, 1.2 mmol, 30 mol %) in solution in toluene (10 ml) is heated at 100° C. for 24 hours. The reaction mixture is cooled to 20° C. and washed with water (10 ml). The organic layer is concentrated to dryness under reduced pressure to afford substantially optically pure (S)-2-(2-oxopyrrolidin-1-yl)butyric acid methyl ester (Ia) (0.54 g, 2.9 mmol, 68%)

GC: retention time=7.89 min

Chiral HPLC: 79.0% (S)/21.0% (R)

6.3. Synthesis of substantially optically pure methyl-(S)-2-(2-oxopyrrolidin-1-yl)butyrate (Ia) (compound (I) with $R^1$=H. $R^2$=Et, X=COOMe) starting from (IIc)

6.3.1. Synthesis of methyl-(R)-4-[(1-methoxycarbonyl)propylamino]butyrate (VIa)

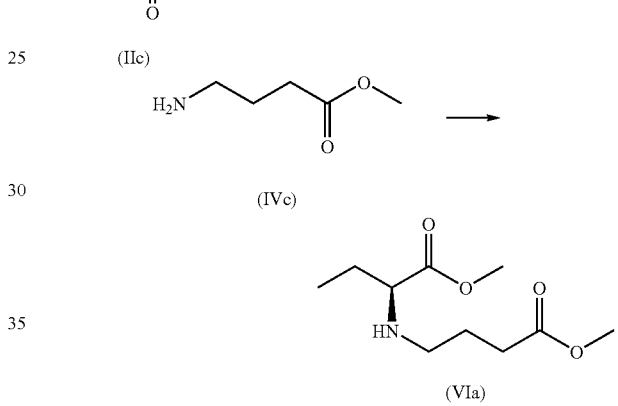

To a solution of methyl-4-aminobutyrate (IVc) (3.68 g, 2.96 mmol, 3 equiv.) in dichloromethane (20 ml, 10 vol.) is added sodium methoxide (4 ml of a 5.4 M solution in methanol, 21.2 mmol, 2.65 equiv.) at room temperature. The mixture is cooled to 0° C. and methyl-(R)-2-trifluoromethanesulfonyloxybutyrate (IIc) (2.0 g, 7.99 mmol, 1 equiv.) is added. The mixture is stirred at room temperature until complete conversion (GC). The reaction mixture is then washed twice with water (2×20 ml) and the organic layer is concentrated under reduced pressure to afford methyl-(R)-4-[(1-methoxycarbonyl)propylamino]butyrate (VIa) as a yellow oil.

The crude product is used directly in the subsequent step.

6.3.2 Synthesis of substantially optically pure (S)-2-(2-oxopyrrolidin-1-yl)butyric acid methyl ester (Ia)

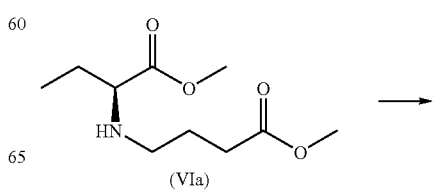

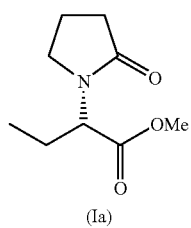

Crude methyl-(R)-4-[(1-methoxycarbonyl)propylamino]butyrate (VIa) is mixed with 2-hydroxypyridine (200 mg, 2.1 mmol, 26 mol %) in toluene (20 ml). The solution is heated at 80° C. until complete conversion. After 48 hours of heating (GC: conversion >95%) the mixture is cooled to 20° C. and washed twice with water (2×20 ml). The organic layer is concentrated to dryness under reduced pressure and affords (S)-2-(2-oxopyrrolidin-1-yl)butyric acid methyl ester as a yellow oil. (1.0 g, 5.4 mmol, 67.5%)

GC: retention time=7.89 min (>90%)
Chiral HPLC: 98.6% (S)/1.4% (R).

Example 7

Synthesis of levetiracetam 7.1. Synthesis of methyl-(S)-4-(J-carbamoylpropylamino)butyrate (VId) (compound (VI) with $R^1$=H. $X^1$=CONH2, $R^2$=Et, $X^2$=COOMe)

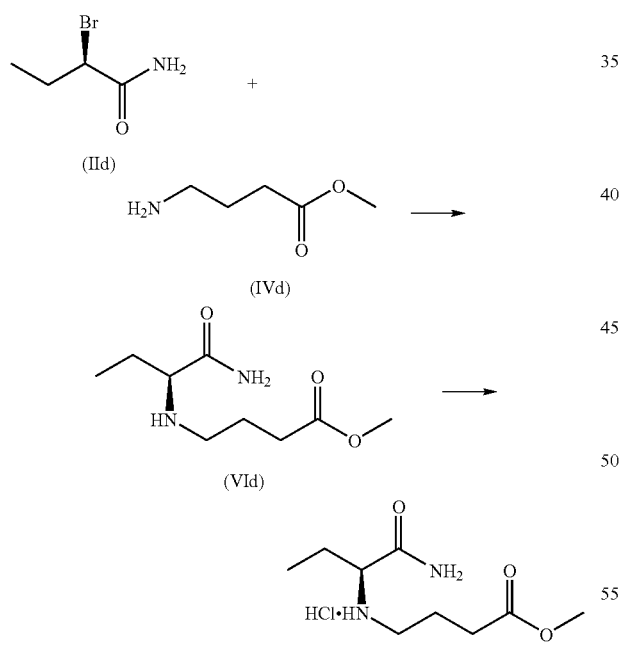

A mixture of (R)-2-bromobutyramide (optical purity >99.5%; 1.0 g, 6.0 mmol), potassium carbonate (4.2 g, 30 mmol, 5 equiv.) and methyl-4-aminobutyrate hydrochloride (1.84 g, 12 mmol, 2 equiv.) is diluted in 15 ml (15 vol.) of acetonitrile and heated at 58° C. for until complete conversion. After 41 hours (GC: 100% conversion), the mixture is cooled to room temperature and filtered. The cake is rinsed with acetonitrile (50 ml) and the combined filtrates are concentrated to dryness under reduced pressure. The residue is taken up with 20 ml of isopropyl acetate and a mixture of HCl solution in dioxane (7 ml) and methanol (7 ml) is added. The hydrochloride salt of methyl-4-(1-carbamoylpropylamino)butyrate (VId) is collected by filtration (0.7 g, 2.9 mmol, 49%).

GC: retention time=9.96 min (100%)
1H NMR δH of the hydrochloride salt (400 mHz, DMSO-d6): 0.89 (3H, t, J 7.4), 1.75-1.92 (4H, m), 2.41-2.46 (2H, m), 2.80-2.85 (2H, m), 3.60 (3H, s), 3.66-3.71 (1H, m), 7.74 (1H, s), 8.09 (1H, s), 8.83, 1H, brs), 9.30 (1H, brs).

7.2. Synthesis of levetiracetam

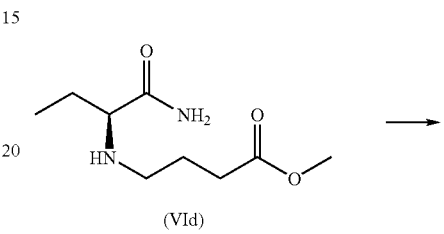

Hydrochloride salt of methyl-4-(1-carbamoylpropylamino)butyrate (VId) (0.7 g, 2.9 mmol) is dissolved in a mixture of tetrahydrofuran (10 ml) and triethylamine (0.6 g, 2 equiv.). The suspension is filtered and filtrates are concentrated to dryness to afford an oil. The resulting residue is dissolved in toluene (15 ml) and 2-hydroxypyridine (53 mg, 0.56 mmol, 20 mol %) is added. The mixture is heated to 80° C. until complete conversion. After 3 days (GC: 100% conversion) the mixture is concentrated to dryness under reduced pressure.

GC: retention time=9.40 min (100%)
Chiral HPLC: 98.6% (S)/1.4% (R)

Example 8

Synthesis of (R)-2-(2-oxopyrrolidin-1-yl)butyramide 8.1. Synthesis of methyl-(R)-4-(1-carbamoylpropylamino)butyrate (VIe) (compound (VI) with $R^1$=H. $X^1$=CONH_2, $R^2$=Et, $X^2$=COOMe)

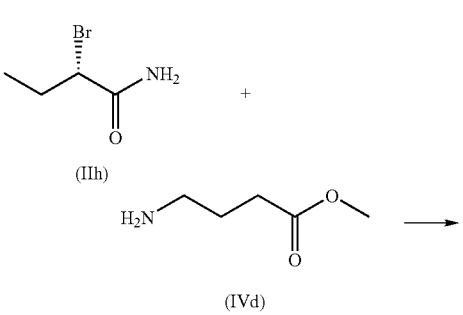

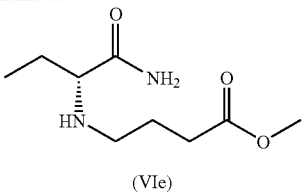

A mixture of (S)-2-bromobutyramide (IIh) (optical purity>98.4%; 0.25 g, 1.5 mmol), potassium carbonate (1.1 g, 8.0 mmol, 5 equiv.) and methyl-4-aminobutyrate hydrochloride (0.46 g, 3.0 mmol, 2 equiv.) is diluted in 5 ml (15 vol.) of acetonitrile and heated at 60° C. for until complete conversion. After 43 hours (GC: >90% conversion), the mixture is cooled to room temperature and filtered. The cake is rinsed with acetonitrile (20 ml) and the combined filtrates are concentrated to dryness under reduce pressure. The crude product is used directly in the subsequent step.

8.2. Synthesis of (R)-2-(2-oxopyrrolidin-1-yl)

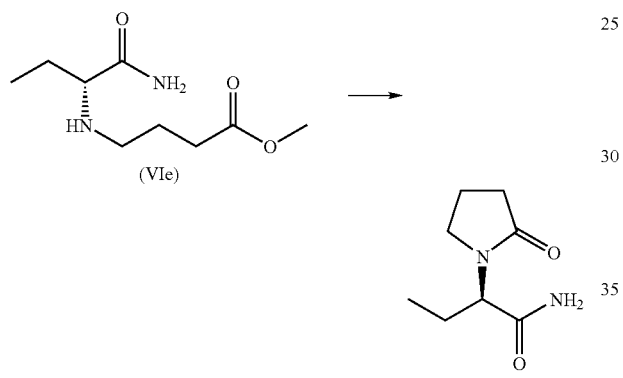

Crude methyl-(R)-4-(1-carbamoylpropylamino)butyrate (VIe) is dissolved in 10 ml of toluene and 2-hydroxypyrridine (14 mg, 10 mol %) is added. The mixture is stirred for 24 hours at 80° C. and then concentrated to dryness to result in 0.621 g of an oil. GC assay showed 40.2%, which corresponds to 0.248 g of (R)-2-(2-oxopyrrolidin-1-yl)butyramide (1.45 mmol, 97%).

Chiral HPLC: 12.7% (S)/87.3% (R)

Example 9

Synthesis of (R)-2-(2-oxopyrrolidin-1-yl)butyramide 9.1. Synthesis of methanesulfonic acid (R)-1-carbamoyl-propyl ester (IIi) (compound (II) with $R^2$=Et, $X^1$=CONH$_2$, Y=OMes)

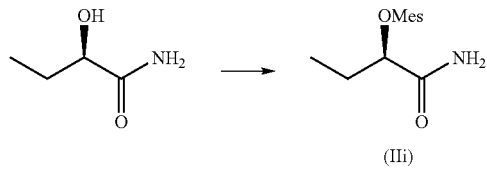

To a mixture of (R)-2-hydroxybutyramide (4.2 g, 40.7 mmol) and triethylamine (6.2 ml, 44.8 mmol, 1.1 equiv.) in tetrahydrofuran (50 ml) is added drop wise at −40° C. methanesulfonic acid chloride (3.5 ml, 44.8 mmol, 1.1 equiv.). The mixture is allowed to warm to 20° C. and is filtered over magnesium sulfate (8 g). The cake is rinsed twice with tetrahydrofuran (2×20 ml) and combined filtrates are concentrated to dryness under reduced pressure to afford methanesulfonic acid (R)-1-carbamoyl-propyl ester (IIi) as a solid. (7.9 g, 106%, triethylamine hydrochloride salts are present).

1H NMR δH (400 mHz, DMSO-d6): 0.89 (3H, t, J 7.4), 1.71-1.92 (2H, m), 3.22 (3H, s), 4.76 (1H, t, J6.1), 7.45 (1H, s), 7.60 (1H, s).

9.2. Synthesis of ethyl-(R)-4-(1-carbamoylpropylamino)butyrate (VIf) (compound (VI) with $R^1$=H. $X^1$=CONH2, $R^2$=Et, $X^2$=COOMe)

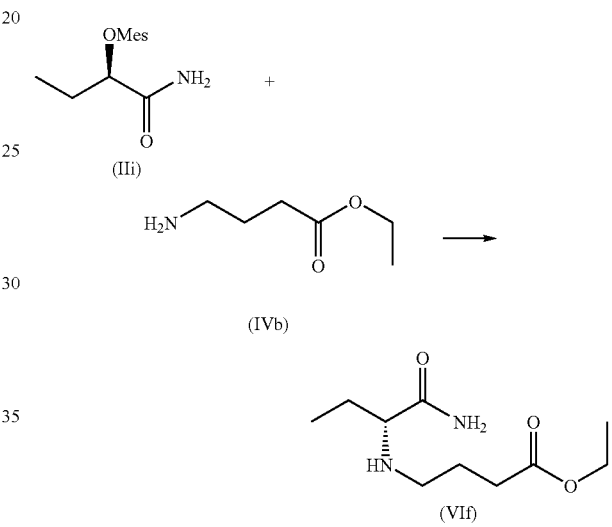

A mixture of powdered caesium carbonate (9.0 g, 27.4 mmol, 5 equiv.), ethyl-4-aminobutyrate (IVb) (1.85 g, 11.0 mmol, 2 equiv.) and methanesulfonic acid (R)-1-carbamoyl-propyl ester (IIi) (1.0 g, 5.5 mmol, 1 equiv.) in acetonitrile (20 ml, 20 vol.) is heated to 60° C. for 16 hours. The mixture is then filtered and the cake rinsed with acetonitrile (50 ml). Combined filtrates are concentrated to dryness under reduced pressure. The crude methyl-(R)-4-(1-carbamoylpropylamino)butyrate is used directly in the next step.

GC: retention time=10.37 min. (100%)

9.3. Synthesis of (R)-2-(2-oxopyrrolidin-1-yl)butyramide

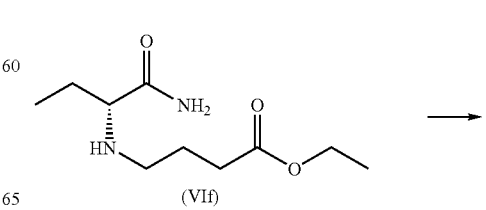

To the crude methyl-(R)-4-(1-carbamoylpropylamino)butyrate (VIf) in toluene (20 ml) is added 2-hydroxypyrridine (50 mg, 10 mol %). The mixture is heated to 80° C. until complete conversion. After 16 hours (GC: 100% conversion) the mixture is concentrated to dryness to yield (R)-2-(2-oxopyrrolidin-1-yl)butyramide (0.28 g, 1.6 mmol, 30%, yield determination by GC assay from pure standard).

Chiral HPLC: 6.0% (S)/94.0% (R)

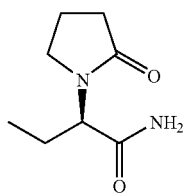

Example 10

Synthesis of levetiracetam

10.1. Synthesis of ethyl-(S)-4-(1-carbamoylpropylamino)butyrate (VIg) (compound (VI) with $R^1$=H, $X^1$=CONH$_2$, $R^2$=Et, $X^2$=COOMe)

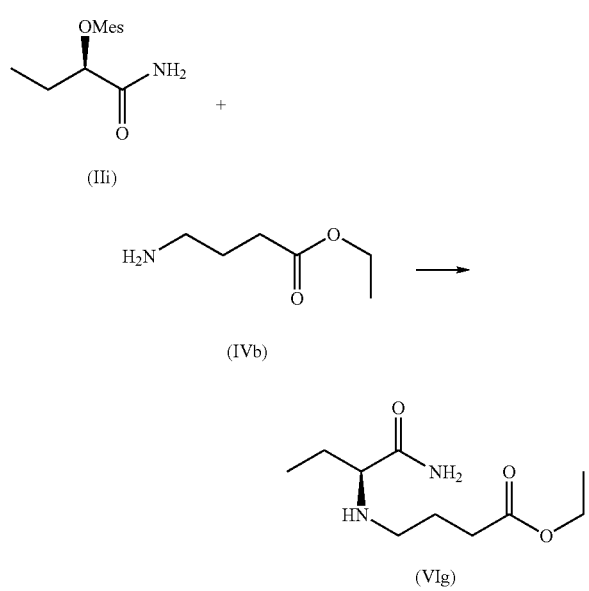

A mixture of powdered potassium carbonate (14.0 g, 96.2 mmol, 5 equiv.), ethyl-4-aminobutyrate (IVb) (6.5 g, 38.6 mmol, 2 equiv.) and methanesulfonic acid (R)-1-carbamoylpropyl ester (IIi) (3.5 g, 19.3 mmol, 1 equiv.) in acetonitrile (40 ml, 11 vol.) is heated to 80° C. for 17 hours. The mixture is then filtered and the cake rinsed with acetonitrile (30 ml). Combined filtrates are concentrated to dryness under reduced pressure. The crude methyl-(S)-4-(1-carbamoylpropylamino)butyrate (VIg) obtained as a yellow oil is used directly in the next step.

GC: retention time=10.37 min. (100%)

10.2. Synthesis of (S)-2-(2-oxopyrrolidin-1-yl)butyramide

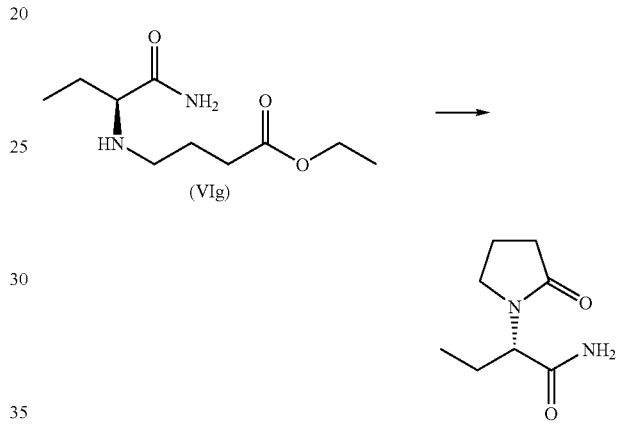

To the crude methyl-(S)-4-(1-carbamoylpropylamino)butyrate (VIg) in toluene (25 ml) is added hydroxypyrridine (0.7 g, 30 mol %). The mixture is heated to 92° C. until complete conversion. After 17 hours the mixture is concentrated to dryness to yield (S)-2-(2-oxopyrrolidin-1-yl)butyramide.

GC: 100% conversion

Chiral HPLC: 79.0% (S)/21.0% (R)

Example 11

Synthesis of (S)-2-[4-propyl-2-oxopyrrolidin-1-yl]butyramide (Ix) (Compound (I) with $R^1$=n-propyl, $R^2$=Et, X=CONH$_2$)

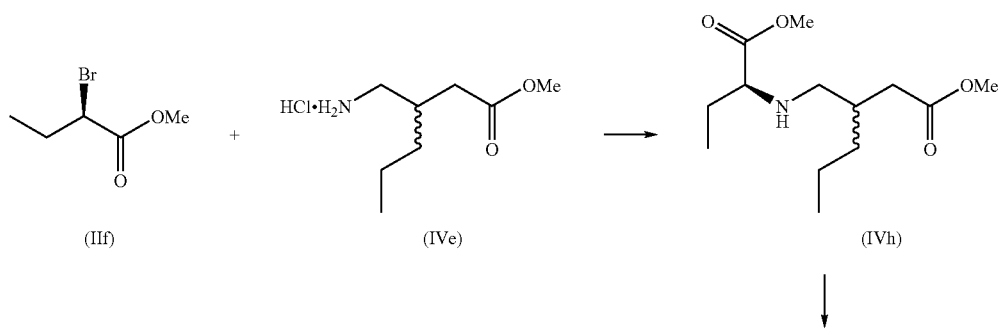

-continued

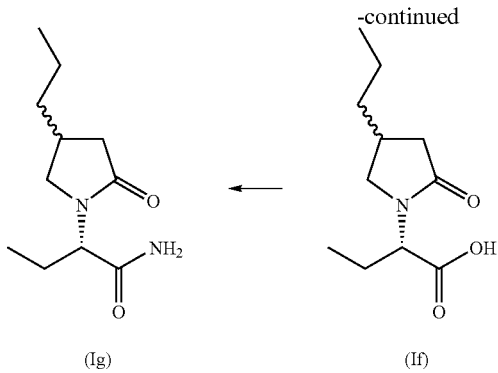

(Ig) (If)

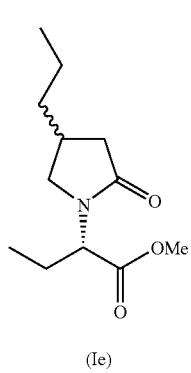

(Ie)

A mixture of powdered potassium carbonate (3.8 g, 27.6 mmol, 5 equiv.), ethyl-4-amino-3-propyl butyrate (IVe) (1.65 g, 8.3 mmol, 1.5 equiv.) and substantially optically pure (S)-2-bromo butyric methyl ester (IIf) (1.0 g, 5.5 mmol, 1 equiv.) in acetonitrile (25 ml, 25 vol.) was stirred overnight at room temperature. The resulting mixture was filtered and the filtrate evaporated to dryness leading to the intermediate (VIh) as yellow oil. The crude residue was dissolved in toluene (20 ml) and 0.1 g of hydroxypyrridine was added. The resulting solution was heated at 80° C. overnight. After cooling to room temperature, 5 ml of a 1M NaOH solution were added and toluene was evaporated under reduced pressure. The resulting aqueous solution was washed with ethyl acetate (2×20 ml) and acidified to pH=2 by addition of a 1N HCl solution. The acidic aqueous solution was extracted twice with 20 ml of ethyl acetate. The combined organic layers were dried (MgSO$_4$) and concentrated to dryness leading to crude acidic intermediate (If). The latter was dissolved in THF (10 ml) and triethylamine was added. The resulting solution was cooled to 0° C. and 0.2 ml of ethychloroformate was added. The mixture was stirred 1 h and 0.5 ml of liquid ammonia was added at room temperature followed by K$_2$CO$_3$ (0.24 g, 1.7 mmol) and 1M aqueous HCl (12 ml). The reaction mixture was extracted twice with ethylacetate (2×20 ml), and combined organic layers were dried (MgSO$_4$) and evaporated leading 0.38 g (1.8 mmol, 32%) of (S)-2-[4-propyl-2-oxopyrrolidin-1-yl]butyramide (Ig).

Chiral HPLC: 44.34%/40.49%/7.73%/7.44%

The invention claimed is:

1. A process for the preparation of a compound of formula (I),

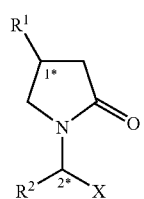
(I)

wherein the compound of formula (I) is substantially diastereoisomerically pure with respect to stereogenic centers 1* and 2*, and
$R^1$ is $C_{1-10}$ alkyl or $C_{2-6}$ alkenyl
$R^2$ is $C_{1-10}$ alkyl or $C_{2-6}$ alkenyl,
X is —CONR$^4$R$^5$, —COOH, —COOR$^3$ or —CN,
$R^3$ is $C_{1-10}$ alkyl;
$R^4$ is hydrogen or $C_{1-10}$ alkyl;
$R^5$ is hydrogen or $C_{1-10}$ alkyl;

which process comprises
(a) reacting a substantially optically pure compound of formula (II),

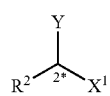
(II)

wherein
$X^1$ is —CONR$^4$R$^5$, —COOH, —COOR$^3$ or —CN
Y is a leaving group selected from halogen, sulfonate group or —N$_2^+$,
with a compound of formula (IV) substantially optically pure at stereogenic center 3*, or salts thereof,

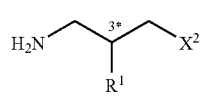
(IV)

wherein $X^2$ is —CONR$^4$R$^5$, —COOH, —COOR$^3$ or —CN;
in a solvent selected from methanol, isopropanol, tert-butanol, dimethoxyethane, dimethylsulfoxide, dichloromethane, acetonitrile, toluene, and mixtures thereof and in the presence of a base selected from potassium hydride, sodium hydride, sodium methoxide, potassium methoxide, sodium isopropoxide, sodium tert-butoxide, potassium tert-butoxide, potassium carbonate, sodium carbonate, triethylamine, cesium carbonate, and triisopropylamine; and
(b) converting the reaction product of II and IV into the compound of the formula I.

2. The process according to claim 1 wherein R$^1$ is $C_{1-4}$ alkyl or $C_{2-4}$ alkenyl.

3. The process according to claim 1 wherein R$^2$ is $C_{1-4}$ alkyl.

4. The process according to claim 1 wherein X and X$^1$ are —CONR$^4$R$^5$.

5. The process according to claim 1 wherein Y is a halogen or a sulfonate group.

6. The process according to claim 1 wherein the conversion of the reaction product of II and IV into the compound of formula I comprises cyclization of a compound of formula (VI),

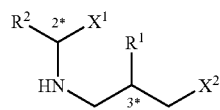
(VI)

wherein
- $R^1$ is hydrogen, $C_{1-10}$ alkyl or $C_{2-6}$ alkenyl;
- $R^2$ is $C_{1-10}$ alkyl or $C_{2-6}$ alkenyl;
- $X^1$ is —CONR$^4$R$^5$, —COOH, —COOR$^3$ or —CN;
- $X^2$ is —CONR$^4$R$^5$, —COOH, —COOR$^3$ or —CN;
- $R^3$ is $C_{1-10}$ alkyl.

7. The process according to claim 1 wherein when X=CONH$_2$ and $X^1$ is COOR$^3$ or COOH, the conversion of the reaction product of II and IV into the compound of formula I comprises ammonolysis of a compound of formula (V),

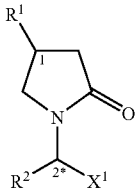

(V)

wherein
- $R^1$ is $C_{1-10}$ alkyl or $C_{2-6}$ alkenyl;
- $R^2$ is $C_{1-10}$ alkyl or $C_{2-6}$ alkenyl;
- $X^1$ is COOR$^3$ or COOH; and
- $R^3$ is $C_{1-10}$ alkyl;

in the presence of water.

8. The process according to claim 1 wherein
- $R^1$ is n-propyl or 2,2-difluorovinyl;
- $R^2$ is ethyl;
- X is —CONH$_2$;
- $X^1$ and $X^2$ are —CONH$_2$, COOH or COOMe; and
- Y is bromine, methanesulfonate or trifluoromethanesulfonate.

9. The process according to claim 1 wherein compound of formula (I) is brivaracetam.

10. The process according to claim 1 wherein compound of formula (I) is seletracetam.

* * * * *